United States Patent [19]

Patrick et al.

[11] Patent Number: 5,163,979
[45] Date of Patent: Nov. 17, 1992

[54] PRESSURE PROGRAMMABLE GAS CHROMATOGRAPH REGULATOR

[75] Inventors: Donald W. Patrick; Richard A. Wolcott, both of Midland, Mich.

[73] Assignee: The Dow Chemical Company, Midland, Mich.

[21] Appl. No.: 722,035

[22] Filed: Jun. 27, 1991

[51] Int. Cl.⁵ .................... B01D 15/08; G01N 30/02
[52] U.S. Cl. .......................................... 55/21; 55/67; 55/197; 55/386; 73/23.36
[58] Field of Search ............ 55/21, 67, 197, 386; 73/23.35, 23.36, 61.1 C

[56] References Cited

U.S. PATENT DOCUMENTS

| | | | |
|---|---|---|---|
| 3,250,057 | 5/1966 | Clarke | 55/197 X |
| 4,035,168 | 7/1977 | Jennings | 55/197 X |
| 4,038,053 | 7/1977 | Golay | 55/197 X |
| 4,479,380 | 10/1984 | Novotny et al. | 73/61.1 C |
| 4,500,432 | 2/1985 | Poole et al. | 55/386 X |
| 4,760,732 | 8/1988 | Bredeweg et al. | 73/23.1 |
| 4,814,089 | 3/1989 | Kumar | 210/659 |
| 4,871,453 | 10/1989 | Kumar | 210/198.2 |
| 4,994,096 | 2/1991 | Klein et al. | 55/197 X |
| 5,032,151 | 7/1991 | Klein et al. | 55/386 X |

FOREIGN PATENT DOCUMENTS

WO90/09585  8/1990  PCT Int'l Appl. .............. 55/386

OTHER PUBLICATIONS

"CGC Using a Programmable Electronic Pressure Controller", B. W. Hermann et al., Journal of High Resolution Chromatography, vol. 13, pp. 361-365 (May 1990).
"CGC Using a Programmable Electronic Pressure Controller", B. W. Hermann et al., 10th International Symposium on Capillary Chromatography, pp. 1001-1009, May 19, 1989.
"Optimized Flow Programming for Temperature-Programmed Gas Chromatography", G. J. Dodo et al., Journal of Chromatography, vol. 328, pp. 49-53, 1985.
"Applications of a Computerized Flow Programmer for Capillary Column Gas Chromatography", S. Nygren et al., Anal. Chem., vol. 57, pp. 2748-2751, (1985).
"Flow Programming of Short Capillary Columns", A. Nohl, Chromatography Review, vol. 11, No. 3, pp. 10-11 (Oct. 1984).
"Exponential Flow Programming and Gas Chromatography", S. Nygren, Journal of Chromatography, vol. 142, pp. 109-116 (1977).
"Flow Programming in Glass Capillary Column Electron Capture Gas Chromatography by Using the Valve in the Splitter Line", S. Nygren et al., Journal of Chromatography, vol. 123, pp. 101-108, (1976).
"Flow Programming and Combined Gas Chromatography—Mass Spectrometry", M. A. Grayson et al., Analytical Chemistry, vol. 45, No. 2, pp. 373-376 (1973).
Brochures—Proportion-Air BB1.
Brochures—Proportion-Air BB2.

Primary Examiner—Robert Spitzer
Attorney, Agent, or Firm—Clement H. Luken, Jr.; David S. Stallard

[57] ABSTRACT

A pressure control apparatus includes an oscillating electronic back pressure regulator connected to a pneumatic or diaphragm-operated back pressure regulator. These are connected to a separation column for effecting a predetermined program of pressure change and thereby improving quantitation of results as well as service life of the regulator.

16 Claims, 2 Drawing Sheets

PRESSURE PROGRAMMABLE GAS CHROMATOGRAPH REGULATOR

FIELD OF THE INVENTION

The invention relates to improvements in the flow regulator apparatus employed in pressure programmable gas chromatography.

BACKGROUND OF THE INVENTION

A wide variety of applications relating to chemistry involve the characterization and identification of the substances constituting multi-component blends, from laboratory research samples to large-scale reaction products which ultimately become commodity and specialty chemicals. To facilitate analysis, these blends generally are combined with a solvent component for dissolving components in the blend and diluting the blend to form a homogeneous multi-component mixture. One technique which is commonly used to separate these mixture components for analysis is gas chromatography.

In a gas chromatograph, components of a multi-component mixture are separated to aid in determining the chemical composition of the components and the quantity of each by sampling the components using a detector such as a flame ionization detector. Separation of the various components is effected by introducing the vaporized mixture by means of a carrier gas onto a column provided with either a solid stationary phase or a liquid stationary phase supported on an inert solid matrix. The sample components in the gaseous phase differ in their tendency to either adsorb onto the solid stationary phase, or to dissolve in the stationary liquid phase. When the carrier gas and vaporized sample are forced through the column, the rate of movement of the various components of the sample depends upon their tendency to either adsorb onto that solid phase or dissolve in that liquid phase. If the component is readily adsorbable or soluble in the particular solid or liquid stationary phase, the component will elute or pass slowly from that phase. On the other hand, if the component is only marginally adsorbable or soluble in the particular stationary phase, it will move rapidly through the column.

As the blend passes through the column, and as a result of the differing adsorption or solubility rates, the vaporized mixture of components eventually separates into a plurality of serially discrete gaseous "plugs" of pure single components; or, in other words, into a train of plugs, each having a homogeneous composition of one of the components to be analyzed. A detector, such as a flame ionization detector, registers the time elapsed from injection of the mixture to the passage of the respective components through the column by causing a deflection in the shape of a bell curve on a moving chart as a plug of pure gaseous component passes over the detector. Thus, a qualitative rendering corresponding to the elution of the component is obtained.

It is desirable, further, that the amount or quantity of the component of the mixture be determined. This is typically obtained by measuring the area under the bell curve.

Action of the carrier gas alone does not cause efficient elution of all the mixture components from the stationary phase. The typical means for facilitating elution is to also adjust the temperature of the column as the run progresses, beginning at a base temperature and increasing linearly over time to the final temperature to aid in removing the components from the stationary phase so that the separation can be completed in a reasonable time. The base temperature, final temperature and rate of increase are all separately adjustable prior to the run. At the final temperature, all the components should be removed from the stationary phase. Typically, the flow rate of the carrier gas during the run remains constant.

There are certain problems associated with temperature programmable chromatography, where the temperature, for example, is increased at a linear rate, or "ramped" up from a base temperature. First, easily decomposable components may be destroyed within the column as the temperature increases. Also, once the unit has reached the final temperature, any subsequent run cannot be conducted until the column has cooled to the base temperature. Further, the evaporation rate of the stationary liquid phase in the column changes exponentially with temperature, thus leading to accelerated degradation of the column at high temperatures.

As an alternative method, separation may be accomplished by adjusting the pressure of the carrier gas as the run progresses while maintaining a generally constant temperature. There are certain advantages to this type of separation method. First, compounds having high boiling points are able to be eluted at relatively low column temperatures. Also, the column lifetime is extended relative to a column subjected to temperature ramping. Further, the evaporation rate of the stationary liquid phase changes only linearly with flow rate compared with an exponential change in a temperature ramped device, the flow rate varying approximately linearly with the changes in pressure encountered in the gas chromatograph. Easily decomposable compounds can be analyzed with less risk of destruction. Finally, the turnaround time is improved because the pressure can be cycled back to the base value more quickly than temperature, thus allowing more efficient use of instrument time.

As with temperature-adjustable gas chromatography, the pressure can be linearly varied with time, or "ramped". One type of pressure ramped gas chromatography involves use of a procedure known as split injection. Depending on the diameter of the column, the gas chromatograph may process the entire volume of sample mixture which is injected, or alternatively may require only a portion of that sample mixture and vent the remainder. The latter technique is known as split injection. Split injection is particularly useful in gas chromatographs utilizing low cross-sectional area columns having inside diameters in the range of 50 to 320 microns (ID), known as capillary columns. The means to ramp the pressure will be described below.

Where it is desired to determine the actual quantity of each component in the sample mixture using the split injection technique, one must maintain a constant ratio for the amount of sample mixture in the column to that amount which is vented. One problem encountered in split injection pressure ramped chromatography is the inability to obtain data to precisely quantitate the amounts of each component separated within the column. It is imperative for quantitation that the pressure within the column at the time of sample mixture injection varies solely in response to the contribution of the sample mixture injected onto the column. Therefore, the pressure regulator unit for the gas chromatograph is generally downstream of the sample injection point, thereby acting as a back pressure regulator. The goal in split injection pressure-ramped gas chromatography is to maintain a constant flow rate during vaporization. To adjust the pressure within the column, it is known to use an adjustable pressure regulator having a needle valve. Though controlled flow is obtained with this type of regulator, one eventually experiences the problem that the needle valve tends to become plugged after a number of successive runs, resulting in varying rates of flow which cause unreliable results. The plugged valve must then be cleaned or replaced.

It is possible to utilize a back pressure regulator having a flat seat and valve plunger wherein the pressure is adjusted by oscillating the valve plunger at varying frequencies to vary the amount of contact with the valve seat. Thus, the plunger is maintained apart from the valve seat for a longer period of time at the low pressure end of the ramp, and maintained in contact with the seat for longer periods at the high pressure end of the ramp. The regulator's pressure response time is improved by controlling the oscillation electronically. This regulator is known as an oscillating electronic back pressure regulator (OEBPR).

As noted above, an OEBPR regulates pressure by adjusting the oscillation rate of a plunger making contact with a valve seat. In the case where the pressure within the tubing rises rapidly due to vaporization of the mixture at the injector, the OEBPR attempts to compensate for the build-up by adjusting the oscillation frequency. However, the pressure increase due to vaporization and subsequent adjustment by the OEBPR results in pressure fluctuation in the gas chromatograph in the vicinity of the injector outlet and the vent. In split injection chromatography, this fluctuation ultimately results in a loss of precision in quantifying the component amounts present as they travel through the column and pass over the detector. In other words, the vagaries of the response time of the OEBPR may result in an indeterminate amount of sample loss, adversely affecting chromatograph sample vaporization accuracy, i.e., OEBPR response time is too slow to avoid significant unknown sample loss. In addition, due to the oscillating nature of the OEBPR, pressure pulses are observable in the injector area which translate to small changes in the actual split ratio in the injector during sample injection. The split ratio is defined as the ratio of the actual flow diverted to a vent divided by the actual flow in the column. The small changes in the split ratio are due to pressure pulses in the injector which reduce the reproducibility, or precision, of repetitive injections of a given sample.

It is therefore an object of the invention to provide an improved pressure regulator apparatus for a pressure programmable gas chromatograph having reduced risk of plugging, but without indefinite undue sample loss.

It is yet a further object of the invention to provide an improved pressure regulator apparatus for a pressure programmable gas chromatograph where undesirable pressure fluctuations are substantially eliminated.

It is yet a further object of the invention to provide an improved pressure programmable gas chromatograph with improved component quantitation and reduced tendency of regulator valve plugging.

It is yet a further object of the invention to provide an improved method for effecting pressure programmable gas chromatography.

SUMMARY OF THE INVENTION

In a preferred embodiment of the present invention, an OEBPR is operably combined with a fixed pressure regulator (pneumatic back pressure regulator or PBPR) in a way to avoid the plugging of the needle valve while also avoiding the effects of a vague or slow OEBPR response time with resulting pressure pulsations during sample injection. This provides the benefits of each regulation format while respectively cancelling out the noted disadvantages of each. The instantaneous pressure fluctuations are eliminated while also allowing the pressure ramped chromatograph to operate with substantial reduction of plugging of the valve seats of the regulators. Pressure is controlled within the chromatograph column initially by the PBPR, which is set at a pressure about 1-5 psi above the initial set point of the upstream OEBPR. Under these pressure adjustment conditions, the OEBPR plunger initially remains out of contact with the valve seat and does not oscillate. Therefore, there are no fluctuations within the injector because the OEBPR has no effect on the regulation of pressure at this point. After sample injection is completed, the OEBPR ramp is initiated. The ramp program adjusts the oscillation of the OEBPR to continuously increase the pressure within the column at a preset rate. Oscillation will begin at a pressure equal to or slightly greater than the set point for the pneumatic unit. Once the oscillating electronic regulator assumes control of the pressure, the pneumatic unit is no longer the most restrictive back pressure controller for the column and thus has a minimal effect on the pressure at the injector during the remainder of the run. Since the OEBPR does not assume an active role until after the sample has been vaporized at the injector, initial fluctuation and undue sample loss caused by the response characteristics of the OEBPR is eliminated.

These and other objects and advantages of the invention will be even more readily apparent from the following detailed description and from the drawings, in which:

DETAILED DESCRIPTION OF THE INVENTION

In its broader aspects a preferred embodiment of the invention relates to a pressure regulator apparatus for a pressure programmable gas chromatograph comprising the combination of an oscillating back pressure regulator operably connected to a diaphragm-operated back pressure needle-valve regulator for effecting a selected program of pressure change with reduced needle-valve clogging and improved sample vaporization precision due to reduced pressure regulator fluctuation. The combination of the oscillating back pressure regulator connected to the diaphragm-operated back pressure needle-valve regulator effects pressure change within the gas chromatograph from an initial pressure controlled by the diaphragm-operated back pressure regulator to a final pressure, by incremental increases controlled substantially by the oscillating back pressure regulator and preferably an electronically controlled oscillating back pressure regulator (OEBPR).

Figure 1:
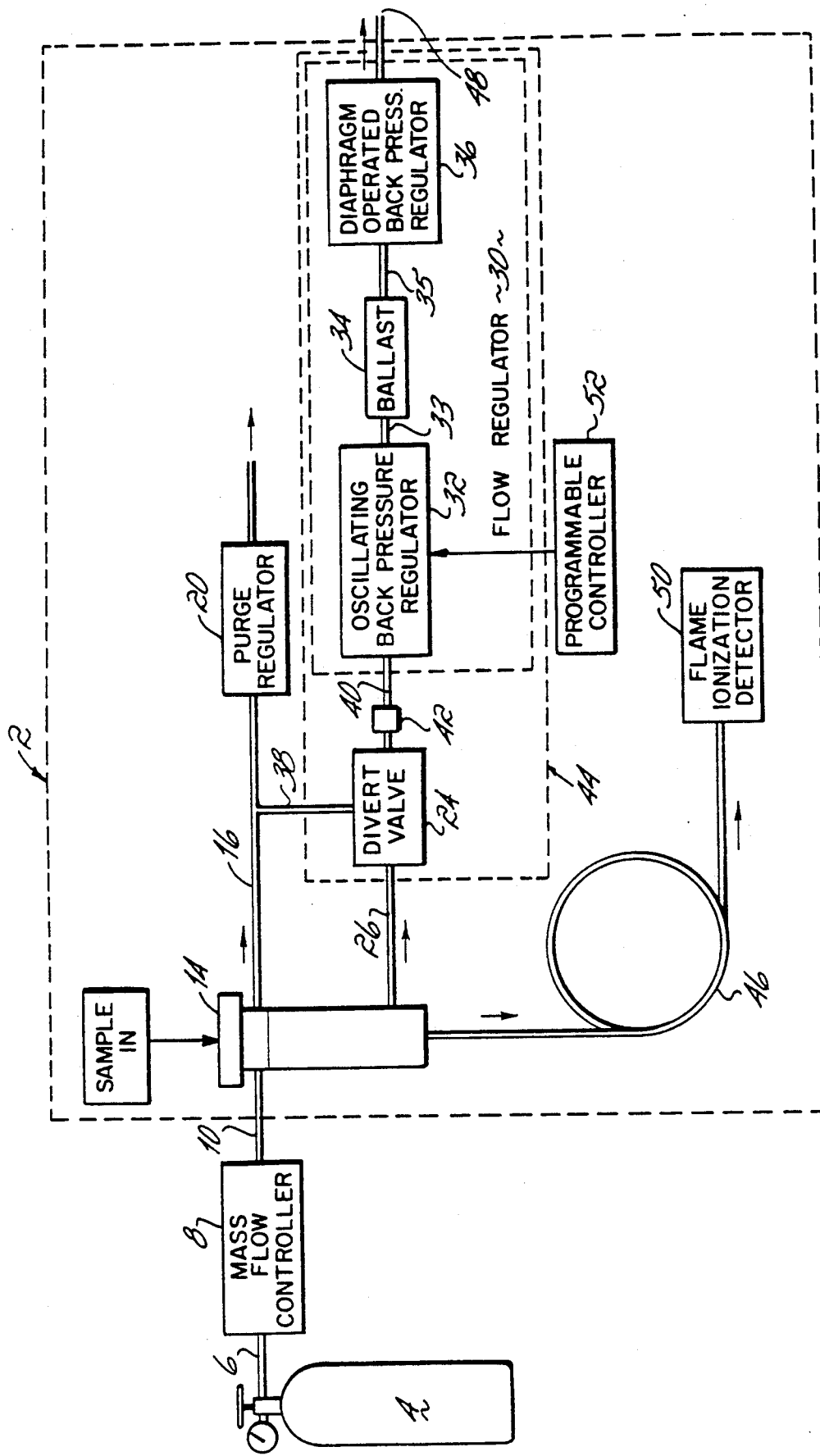
FIG. 1 is a schematic diagram of a gas chromatography system incorporating the improved pressure regulator apparatus of the present invention.

The gas chromatograph 2 shown in FIG. 1, according to the preferred embodiment of the invention comprises an injector 14, flow regulator 30, separation column 46 and flame ionization detector 50. Also included are a purge regulator 20 which controls the septum purge flow, and a divert valve 24 as will be described. A carrier gas flow is supplied to the gas chromatograph 2 via storage bottle 4 or some other suitable source. Carrier gas flows into the gas chromatograph 2 via bottle outlet line 6. The flow is adjusted by the mass flow controller 8. The mass flow controller 8 is of the type produced by the Porter Instrument Company, Inc., Hatfield, Pa., such as the Model VCD 1000 Variable Flow Controller. This controller has a maximum operating pressure of 250 psig (pounds per square inch gauge), a maximum operating temperature of 160° F., and can be fitted with flow elements allowing capacities in the range of 0.5-5.0 cc/min up to 150.0-1500.0 cc/min.

The carrier gas, preferably helium, exits the mass flow controller 8 and enters the gas chromatograph 2 via feed line 10, which conducts the carrier gas to the injector 14. To minimize the risk of column contamination from septum bleed caused by volatilization of lower molecular weight components in the material used to form the septum, a purge line 16 is fitted to the injector 14 upstream of the point in the injector 14 where the injected multi-component mixture is vaporized to conduct a gas flow consisting essentially of carrier gas and the volatilized lower molecular weight septum components, and the pressure within the purge line 16 is controlled by purge regulator 20, such as Hewlett-Packard part No. 19246-605. The feed lines and column tubing within the gas chromatograph 2 are typically manufactured from 316 stainless steel.

Although a sample mixture can be injected manually, injector 14 is preferably connected to any suitable means for introducing a relatively small volume of a mixture into the injector where it is vaporized and combined with the carrier gas for introduction to the separation column 46. Preferably an automatic sample injector, such as the Hewlett-Packard 7673 autosampler, is employed to minimize sample injection variation which can occur if done manually.

Where a capillary column, or other column of narrow cross-section is utilized for component separation, only a portion of the sample mixture injected into injector 14 is necessary for obtaining satisfactory analytical results. In this instance, the vaporized sample mixture aliquot is split, with one portion being fed into the column and the remainder diverted through divert valve 24 and through the flow regulator 30 to a vent opening 48.

FIG. 1 depicts the flow regulator 30 in relation to the gas chromatograph 2. Oscillating electronic back pressure regulator 32 is connected via line 33 to ballast 34, and thence via line 35 to diaphragm-operated back pressure regulator 36. Ballast 34 is a chamber, preferably stainless steel, which serves to partially dampen the fluctuations of pressure within the flow regulator 30. The flow regulator 30 is connected to the divert valve 24 by conduit 40. A 7 micron filter 42 such as the Nupro FW serves to reduce particulates from entering the flow regulator 30. Optionally, the flow regulator 30 can operate without the ballast 34, as will be discussed in more detail below. That portion of the gas chromatograph 2 from divert valve 24 to vent opening 48 is known as the split vent 44. The split vent 44 controls the ratio of the amount of sample conducted into separation column 46 relative to the amount vented to the outside via vent opening 48, and further controls the pressure at the injector 14 via flow regulator 30.

The injector 14 is equipped with heating means (not shown) to vaporize the sample mixture. At least a portion of the vaporized mixture is conducted into the separation column 46. The individual components of the sample are detected by detector means, such as a flame ionization detector 50 of any suitable kind.

The flow regulator 30 operates in the following manner. The OEBPR 32 is initially set at a pressure about 1 to 5 psig lower than that of the diaphragm-operated back pressure regulator 36. Thus, the initial pressure within the gas chromatograph 2 is controlled by the diaphragm-operated back pressure needle-valve regulator 36, the OEBPR being fully opened. After sample is injected into injector 14, and a portion of the sample mixture vapor diverted through valve 24, if necessary, the pressure ramping sequence is begun. When the sample mixture and carrier gas are first introduced into injector 14, and the mixture is vaporized, a high pressure spike is initially created. The initial pressure increase is accommodated by the open needle valve of the PBPR 36, which because it is set at a relatively low pressure has an opening large enough to minimize plugging between cycles. Then, in response to a predetermined electrical control signal, the frequency of oscillation of the plunger within the OEBPR 32 adjusts to thereby increase pressure within the gas chromatograph 2 and facilitate separation of the components of the injected sample. Since the OEBPR 32 takes no active part in regulating pressure at the time of initial sample injection, that regulator does not contribute to any pressure fluctuation within the system during the sample mixture vaporization step. After vaporization is completed and sample mixture is flowing toward the separation column 46, the OEBPR 32 takes control of pressure regulation.

The ballast 34 serves to reduce pressure pulsations downstream of the OEBPR. The ballast is believed to improve the operating lifetime of the PBPR. Optionally, the ballast may be removed from the flow regulator 30 without significant detrimental effect on precision of detection and quantitation of the sample mixture components.

Figure 2:
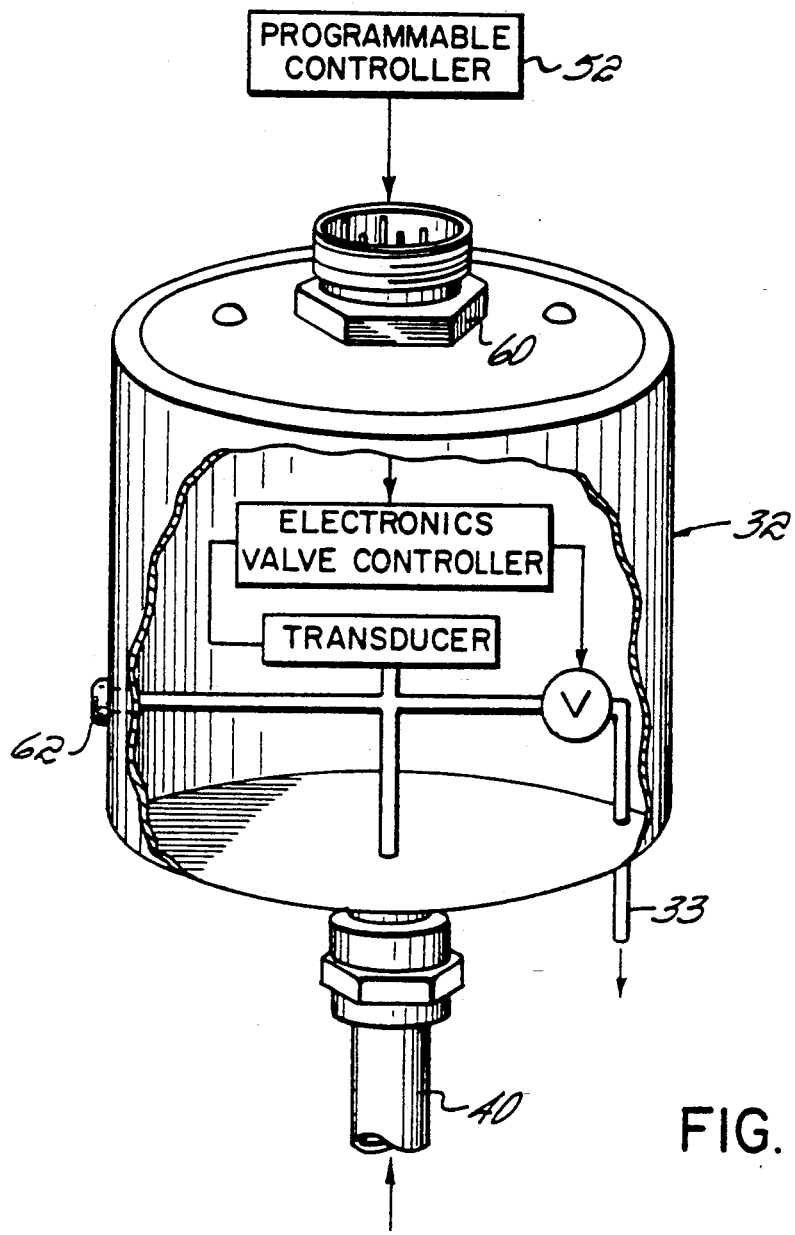
FIG. 2 is an illustrative diagram of the oscillating electronic back pressure regulator of FIG. 1, and illustrating its significant features and connections to other components within the gas chromatograph.

The oscillating electronic back pressure regulator 32 is shown in more detail in FIG. 2. Suitable results have been obtained utilizing an OEBPR made by Proportion Air, McCordsville, Ind. 46055. This regulator, designated the model BB1 MFE100 S46S21 ("BB1"), employs a 5 pin connector 60 at the top of the regulator 32 to control its electrical functions.

As indicated in FIG. 2, the various pins connect to a programmable controller 52 such as that described generally as the "analog electrical circuit 15" in U.S. Pat. No. 4,760,732, which is expressly incorporated herein by reference. The programmable controller 52 supplies a variable control voltage in the range of 0 to 10 V.D.C. to the OEBPR 32 to vary the pressure. The controller 52 includes an electrical ramp generating circuit to cause the OEBPR 32 to pressure ramp. A supply voltage of 15 V.D.C. to operate the OEBPR 32 is also provided by the programmable controller 52. The particular Proportion Air OEBPR can operate with a supply voltage in the range of 15-24 V.D.C.

Other pins connect the OEBPR 32 to analog measurement equipment, and to equipment which reads digital output, if desired. Any suitable controller and measurement equipment can be used. Gas enters the regulator 32 via conduit 40, and exits via connector 33. A separate inlet port marked at 62, is capped since it is not necessary in this application. The model BB1 OEBPR described above has a stainless steel diaphragm pressure transducer which is generally inert to the range of component materials injected into the gas chromatograph 2. Any suitable OEBPR can be used.

The PBPR 36 can be any one of a number of commercially available units which are designed to accommodate the range of chemical compounds, pressures and temperatures encountered in the gas chromatograph. Good results have been obtained from a pneumatic regulator supplied by Hewlett-Packard, and bearing the Part number 19246-60570. This regulator has an operating pressure in the range of 0-30 psig. Another regulator which may be used is the Model 9000 back pressure regulator from the Porter Instrument Company, available in regulating ranges of 0-15, 0-30, 0-60 and 0-100 psig. The Porter regulator has a capacity of 0-1000 sccm.

The divert valve 24 of FIG. 1 permits split injection or splitless injection of samples. The divert valve 24 is a stock component in the Hewlett-Packard 5890 gas chromatograph having a split/splitless capillary inlet. The operation of this valve is not affected by addition of the OEBPR. During split injection, conduit 26 is effectively connected directly to the filter 42 to conduct a split gas flow comprising a major portion of the carrier gas and sample mixture from injector 14. Substantially all of the remainder of the gas flow comprised of the carrier gas and volatilized sample mixture is conducted away from injector 14 into column 46 for analysis. In the split injection mode, the divert valve 24 is set at the control panel (not shown) of the gas chromatograph to permit no gas flow through conduit 38. If splitless injection is used, conduit 26 is terminated at the divert valve 24 during sample injection and conduit 38 is effectively coupled to the filter 42. In this mode, the substantial majority of the sample mixture is vaporized and conducted into column 46. After a specified amount of time after injection determined by the analyst, the divert valve 24 is switched back to the split mode on the Hewlett-Packard instrument to eliminate any residual solvent vapors in the injector 14.

Splitless injection can offer higher sensitivity since the entire sample is injected into the column rather than a small portion, as in split injection. Pressure programming can be used for splitless injection as well as split injection.

Alternatively, a very high initial pressure can be used during the splitless injection followed by a rapid return to a lower pressure for the balance of the chromatographic run as directed by programmable controller 52. This can be accomplished by setting the OEBPR 32 at a pressure higher than the PBPR 36 during splitless injection, followed by either a return to a lower OEBPR pressure that is above the PBPR set point where the OEBPR is still controlling pressure, or a return to an OEBPR pressure that is lower than the PBPR where the PBPR will control pressure.

OPERATING EXAMPLES

The following examples compare the retention time and achievable precision for several different regulator configurations of linear pressure program, split injection capillary gas chromatography on a Hewlett-Packard Model 5890 gas chromatograph. An example utilizing a temperature-ramped program for sample separation and quantitation is included for comparison. Conditions common to the individual working examples were as follows: column dimensions of 15 meter ×0.25 millimeter inside diameter, 0.1 micrometer film DB-5 fused silica open tubular (FSOT) chromatographic column such as that supplied by J & W Scientific, Folsom, Calif.; injector temperature of 200° C.; flame ionization detector maintained at a temperature of 250° C.; Hewlett-Packard 7673 autosampler to reduce sample introduction variables; and a one microliter injection volume consisting of 1000 parts per million each of $n\text{-}C_{12}$, $n\text{-}C_{14}$, $n\text{-}C_{16}$, and $n\text{-}C_{18}$ alkanes in hexane solvent, with 10 injections made for each example.

EXAMPLE 1

Pressure was maintained at 8.9 psig isobaric utilizing a Hewlett-Packard diaphragm-operated back pressure regulator, Part No. 19246-60570. Separation was facilitated by ramping the temperature, beginning at 110° C. and holding for 2 minutes, with temperature increasing incrementally from 110 to 200° C. at a rate of 4° C. per minute. The flow rate was 92 millimeters per minute split flow.

The quantitative results of alkane amounts after 10 repetitive injections is listed below.

TABLE 1

|  | RT X[1] | RT rsd[2] (%) | Area X[3] | Area rsd[4] (%) |
|---|---|---|---|---|
| $n\text{-}C_{12}$ | 1.80 | 0.070 | 16721 | 0.48 |
| $n\text{-}C_{14}$ | 4.00 | 0.001 | 17350 | 0.47 |
| $n\text{-}C_{16}$ | 7.99 | 0.038 | 18254 | 0.41 |
| $n\text{-}C_{18}$ | 12.81 | 0.025 | 18545 | 0.38 |

[1] Average retention time (RT) at peak apex in minutes, for 10 replicate injections.
[2] Relative standard deviation (%), of RT for 10 replicate injections.
[3] Average raw peak area counts for 10 replicate injections.
[4] Relative standard deviation (%) for raw peak area counts for 10 replicate injections.

EXAMPLE 2

In this instance, separation was facilitated by altering pressure and maintaining temperature at a constant level. Pressure regulation was effected by a Proportion Air BB1 oscillating electronic back pressure regulator with a 150 mL stainless steel Hoke pressure vessel ballast connected downstream. A Nupro needle valve (SS-2SG) was connected downstream of the ballast. The needle valve was adjusted to give negligible flow fluctuation of the split vent flow as observed on a Spectrum Model 59 Flowrater (0-150 ml/min. range). Operating temperatures were 110° C. isothermal, with an initial back pressure of 6.7 psig for 2 minutes, followed by a pressure ramp from 6.7 to 43.1 psig at 2.6 psig per minute, with a 90 milliliter/min split flow. The PBPR was not present.

TABLE 2

|  | RT X | RT rsd (%) | Area X | Area rsd (%) |
|---|---|---|---|---|
| $n\text{-}C_{12}$ | 1.75 | 0.301 | 18363 | 2.60 |
| $n\text{-}C_{14}$ | 3.72 | 0.177 | 18874 | 4.66 |
| $n\text{-}C_{16}$ | 7.60 | 0.070 | 20373 | 5.73 |

TABLE 2-continued

| | RT X | RT rsd (%) | Area X | Area rsd (%) |
|---|---|---|---|---|
| n-C$_{18}$ | 15.12 | 0.117 | 21764 | 5.90 |

EXAMPLE 3

In this example, temperature was maintained at 110° C. isothermal. Pressure was ramped to facilitate separation, and the pressure regulator consisted of the Proportion Air BB1 OEBPR, 150 ml Hoke stainless steel pressure vessel ballast, and Hewlett-Packard PBPR connected in order in series, with the OEBPR being furthest upstream. Initial pressure for the Hewlett-Packard PBPR was 7.2 psig, and the BB1 OEBPR pressure set at 5.0 psig and held for 2 minutes. After 2 minutes, the BB1 OEBPR was ramped from 5 to 41.2 psig at a rate of 2.6 psig per minute, and then held at 41.2 psig. A split flow was maintained at a rate of 92 milliliters per minute.

TABLE 3

| | RT X | RT rsd (%) | Area X | Area rsd (%) |
|---|---|---|---|---|
| n-C$_{12}$ | 2.07 | 0.049 | 13182 | 0.59 |
| n-C$_{14}$ | 4.14 | 0.418 | 13659 | 0.60 |
| n-C$_{16}$ | 8.09 | 0.324 | 14599 | 0.59 |
| n-C$_{18}$ | 15.64 | 0.214 | 15400 | 1.22 |

EXAMPLE 4

To determine the effect of the ballast on damping the pressure pulses at the injector during programming, a test was conducted wherein the OEBPR was connected upstream of the pneumatic back pressure regulator and runs made both with and without an intervening ballast, which was the 150 ml Hoke stainless steel pressure vessel ballast. In this case the OEBPR was the model PV1, manufactured by ISI Fluid Power, Fraser, Mich. The column utilized was the same as that noted above. The column oven temperature was maintained at 100° C. isothermal, with the initial pressure of the pneumatic regulator from Hewlett-Packard at 7 psig, and the PV1 OEBPR at 5 psig. The OEBPR pressure was held constant for 2 minutes and then programmed from 5 psig to 45 psig at a rate of 2.8 psig per minute and held at the final pressure of 45 psig for 2 minutes. Detection was by flame ionization detector, at 250° C. The injector was maintained at a temperature of 200° C. The results of the relative standard deviation in peak area for the same blend of normal alkanes in hexane discussed above are provided in the Table below.

TABLE 4

| Regulator Configuration | Relative Standard Deviation of Raw Peak Area (%) | | | |
|---|---|---|---|---|
| | n-C12 | n-C14 | n-C16 | n-C18 |
| With ballast[5] | 1.04 | 1.06 | 1.12 | 1.53 |
| Without ballast[6] | 1.21 | 1.00 | 1.03 | 1.21 |

[5]Ten replicate injections.
[6]Seven replicate injections.

In comparing Examples 2 and 3, it can be seen that substantial improvements in the relative standard deviation of the raw area calculation results by combining the OEBPR and PBPR in series. Retention time data for the two examples were similar. The higher area relative standard deviation for the n-C$_{18}$ component in Table 3 is most likely due to integration errors associated with the band broadening of the peak due to column efficiency losses at the high carrier gas flow rates.

In Example 4, the comparison of regulators with and without ballast demonstrated little change in the peak area relative standard deviation. Thus, the ballast may be removed from the regulator 30 without adverse effect on quantitation properties. However, it is believed that the ballast functions further to reduce pressure pulsations downstream of the OEBPR, and thereby improve the lifetime of the PBPR.

Comparison of Example 3 with the temperature ramped system of Example 1 shows that temperature ramping produces reduced retention time deviation and slightly improved raw area relative standard deviations. However, the temperature ramped system suffers from the disadvantages noted above, i.e., sample mixture component degradation at high temperatures, faster evaporation of the liquid stationary phase in the column, and slower cycling of the gas chromatograph oven when making successive runs.

The foregoing data demonstrate that the improved regulator consisting of the combination of OEBPR and PBPR and optionally the ballast can be successfully employed in gas chromatograph devices to improve both the precision of quantitation of the sample components and the operative lifetime of the regulator.

While the invention has been described in conjunction with specific embodiments thereof, it is evident that many alternatives, modifications, and variations will be apparent to those skilled in the art in light of the foregoing description, and applicant intends to be bound only by the appended claims.

What is claimed is:

1. A method for separating the components of a sample mixture in a pressure programmable gas chromatograph comprising:
    introducing the sample mixture into the gas chromatograph;
    vaporizing said sample mixture introduced into said gas chromatograph;
    combining said sample mixture vaporized in said gas chromatograph with a carrier gas to form a gaseous blend;
    conducting said gaseous blend into a separation column within said gas chromatograph to effect separation of said gaseous blend into components;
    regulating the pressure of said gaseous blend in said column by a regulator apparatus comprising an oscillating back pressure regulator and a diaphragm-operated back pressure regulator; and
    detecting said components of said gaseous blend as each said component exists said separation column.

2. The method of claim 1 wherein said pressure of said gaseous blend is regulated by setting said diaphragm-operated back pressure regulator about 1 to about 5 psi higher than an initial pressure selectively set at said oscillating back pressure regulator.

3. A method of effecting a selected program of pressure change in a pressure programmable gas chromatograph comprising of steps of:
    controlling an initial pressure in a separation column in a pressure programmable gas chromatograph with a first pressure regulator to a first pressure; and
    increasing the pressure in said separation column incrementally with a second pressure regulator to a final pressure greater than said first pressure.

4. The method of claim 3, wherein said step of controlling the initial pressure in said separation column is effected by a diaphragm-operated back pressure regulator.

5. The method of claim 4, wherein said step of increasing pressure in said separation column incrementally is effected by an oscillating back pressure regulator.

6. The method of claim 5, wherein said step of increasing pressure in said separation column incrementally is effected by an oscillating back pressure regulator operably connected between said separation column and said diaphragm-operated back pressure regulator.

7. A pressure regulator apparatus for a pressure programmable gas chromatograph comprising:
the combination of an oscillating back pressure regulator operably connected to a diaphragm-operated back pressure regulator;
said combination being operably connected to a separation column of a pressure programmable gas chromatograph and being operable to effect a selected program of pressure change within said separation column.

8. A pressure regulator apparatus for a pressure programmable gas chromatograph comprising the combination of:
an oscillating back pressure regulator for producing a final pressure in a separation column of a pressure programmable gas chromatograph by incremental increases;
a diaphragm-operated back pressure regulator for controlling an initial pressure in a separation column of a pressure programmable gas chromatograph;
said oscillating back pressure regulator being operably connected to said diaphragm-operated back pressure regulator; and
said oscillating back pressure regulator and said diaphragm-operated back pressure regulator being operably connected to said separation column and in combination, effecting predetermined pressure change therein.

9. An improved pressure regulator apparatus for a pressure programmable gas chromatograph comprising:
means for receiving a sample mixture and carrier gas;
an outlet from said receiving means;
an oscillating back pressure regulator connected to said receiving means upstream of said outlet for adjusting the pressure within said receiving means after a sample mixture has been introduced thereto; and
a diaphragm-operated back pressure regulator connected to said receiving means, upstream of said outlet, for setting the initial pressure inside said receiving means at the time said sample mixture is introduced therein.

10. The apparatus of claim 9 wherein said diaphragm-operated back pressure regulator is operably connected to said receiving means indirectly downstream of said oscillating back pressure regulator.

11. The apparatus of claim 9 wherein said oscillating back pressure regulator is selectively set at an initial pressure and wherein said diaphragm-operated back pressure regulator is set at a pressure higher than the initial pressure of said oscillating back pressure regulator.

12. The apparatus of claim 11 wherein said diaphragm-operated back pressure regulator is set at a pressure in the range of about 1 to about 5 psi higher than the initial pressure of said oscillating back pressure regulator.

13. The apparatus of claim 9 further having a ballast connected to said receiving means.

14. The apparatus of claim 13 wherein said ballast is connected between said oscillating and said diaphragm-operated back pressure regulators.

15. The apparatus of claim 9 wherein said pressure inside said receiving means varies over a range of about 0.5 to about 100 psi.

16. A pressure-programmable gas chromatograph comprising:
sample mixture inlet means;
a pressure regulator apparatus comprising an oscillating back pressure regulator operably connected to a diaphragm-operated back pressure regulator for effecting a selected program of pressure change;
a column for separating components of said sample mixture;
means connecting the mixture inlet means with the column, said pressure regulator apparatus operably connected to said connecting means; and
sample mixture component detection means operably connected to said column.

* * * * *